United States Patent [19]

Zuidam et al.

[11] 4,456,535
[45] Jun. 26, 1984

[54] PROCESS FOR THE REMOVAL OF UREA, AMMONIA, AND CARBON DIOXIDE FROM DILUTE AQUEOUS SOLUTIONS

[75] Inventors: Jan Zuidam, Schimmert; Petrus J. M. van Nassau, Munstergeleen; Pierre G. M. B. Bruls; Kees Jonckers, both of Born, all of Netherlands

[73] Assignee: Unie van Kunstmestfabrieken, B.V., Utrecht, Netherlands

[21] Appl. No.: 325,922

[22] Filed: Nov. 30, 1981

[30] Foreign Application Priority Data

Nov. 28, 1980 [NL] Netherlands ............... 8006477

[51] Int. Cl.³ .................. B01D 3/26; C02F 1/20
[52] U.S. Cl. .................. 210/750; 210/752; 210/766; 210/774; 564/73; 55/38; 55/70
[58] Field of Search ............ 210/750, 774, 766, 752; 564/73; 55/38, 70

[56] References Cited

U.S. PATENT DOCUMENTS 4,341,640  7/1982  Landis ............... 210/774

FOREIGN PATENT DOCUMENTS 146752  3/1981  Fed. Rep. of Germany ...... 210/750
146751  3/1981  Fed. Rep. of Germany ...... 210/750
2058764  3/1981  United Kingdom ............ 564/73

OTHER PUBLICATIONS

E.P.A. Development Document, 440/1-73/011, Nov. 1973, pp. 81 and 103-105.

*Primary Examiner*—Benoit Castel
*Attorney, Agent, or Firm*—Cushman, Darby & Cushman

[57] ABSTRACT

An improved process for the removal of urea, ammonia, and carbon dioxide from dilute aqueous solutions thereof by hydrolyzing the urea, and thereafter desorbing ammonia and carbon dioxide. The dilute solution containing urea is passed into the top portion of a reaction column and caused to flow downward and countercurrent to a heating and stripping gas while maintaining the reaction column at a pressure of between about 10 and 30 bar, and a top column temperature of between about 170° and 220° C. and a bottom column temperature of between about 180° and 230° C. The resulting liquid stream removed from the bottom of the reaction column, comprised of a substantially urea-free aqueous solution of ammonia and carbon dioxide, is introduced into a desorption zone wherein, at a pressure of between about 1 and 5 bar, ammonia and carbon dioxide are removed therefrom.

4 Claims, 1 Drawing Figure

PROCESS FOR THE REMOVAL OF UREA, AMMONIA, AND CARBON DIOXIDE FROM DILUTE AQUEOUS SOLUTIONS

BACKGROUND OF THE INVENTION

This invention relates to a process for the removal of urea, ammonia, and carbon dioxide from dilute aqueous solutions.

In the preparation of urea from ammonia and carbon dioxide at elevated temperatures and pressures, a urea synthesis solution is formed which contains, in addition to product urea, a substantial quantity of free ammonia and non-converted ammonium carbamate. To recover the urea, the ammonium carbamate is first decomposed in one or more pressure steps, into ammonia and carbon dioxide which are then driven out of the solution, together with free ammonia, and usually recirculated. The final decomposition step generally results in an aqueous urea solution which still contains a quantity of dissolved ammonia and carbon dioxide, which are removed by expansion to atmospheric or even lower pressures. The remaining aqueous urea solution is then concentrated by evaporation and/or crystallization and subjected to further processing as required.

During the evaporation of the aqueous urea solution a gas mixture is formed which, in addition to water vapor, contains ammonia, carbon dioxide, and entrained fine droplets of urea. This gas mixture from the evaporation step is condensed, usually together with the gas mixture removed by the expansion of the aqueous urea solution, to atmospheric or lower pressure, and a portion of the process condensate thus obtained is returned to the process. For instance, this process condensate can be used for absorbing the gas mixture driven off in the final decomposition step. The remaining portion of the process condensate is discharged from the process.

This process condensate incorporates the various water streams fed into the process, including the steam used for operating the ejectors in the evaporation section, washing water, and flushing water applied to the stuffing boxes of the carbamate pumps. Additionally, for each mole of urea synthesized, one mole of water is formed. Thus, in a urea plant with a capacity of 1,500 tons of urea per day, 450 tons per day of water are formed. About 300 tons per day of additional water are fed into the process, so that roughly 750 tons of water in total must be discharged from the process.

This process condensate will generally contain approximately 2-9 percent by weight ammonia, 0.8-6 percent by weight carbon dioxide, and 0.3-1.5 percent by weight of urea. This represents important quantities of raw materials and product that ideally should be recovered. Moreover, if it is discharged as such, it would load the surface water into which it is discharged with waste to a degree no longer permitted by the governments of many countries. It is, therefore, necessary to remove a major portion of the ammonia and urea present prior to discharging this process condensate to the environment.

To accomplish this, the process condensate can be subjected to a treatment such as described in Industrial Wastes, September/October, 1976, at pages 44-47, wherein the process condensate, already freed of part of the ammonia and carbon dioxide by desorption at low pressure, is passed at a higher pressure into the bottom of a reaction column. In the reaction column, it is heated by means of steam, also fed into the bottom, resulting in the hydrolysis of the urea present. The solution thus obtained, having a reduced urea content, is removed from the top of the reaction column. In addition to a small quantity of nonhydrolyzed urea, this resulting solution also contains ammonia and carbon dioxide which are removed, after expansion of the solution to a lower pressure, in a second desorption column by stripping with steam. The gas mixture obtained in the second desorption column can be used as the stripping agent in the first desorption column. The bottom product liquid stream from the second desorption column is then discharged from the process after heat exchange with the process condensate to be treated.

Although this known process does succeed in removing the major portion of urea and ammonia from the process condensate, in practice this waste flow discharged into the environment will still contain about 50 ppm ammonia and 50 ppm urea. Furthermore, even with very long residence times, for which inefficiently large reaction columns would be required, it is impossible to reach a urea content lower than about 20-25 ppm.

BRIEF DESCRIPTION OF THE INVENTION

It is the object of the present invention to provide an improved process whereby both the ammonia content and the urea content of this process condensate can be reduced to less than 10 ppm before it is discharged to the environment. This substantially improved removal of urea and ammonia is achieved by passing the dilute solution of urea, ammonia, and carbon dioxide to be treated into the top portion of the reaction column at a temperature and pressure such that a gas phase can be formed, and causing it to flow downward within the reaction column countercurrent to a gas stream passed into the bottom of the reaction column, which gas serves not only as a heating agent but also as a stripping agent.

The invention thus provides an improved process for the removal of urea, ammonia, and carbon dioxide from dilute aqueous solutions by hydrolysis of urea and desorption of the ammonia and carbon dioxide thus formed. Specifically, the dilute aqueous solution is passed into the top portion of the reaction column at a pressure of between about 10 and 30 bar, and is caused to flow downward therein countercurrent to an upflowing gas stream which functions to both heat and strip the solution. To obtain the degree of removal of urea and ammonia from the aqueous solution as contemplated by this invention, the top of the reaction column should be maintained at a temperature of between about 170° and 220° C., and the bottom of the column should be maintained at a temperature of between about 180° and 230° C. A gas mixture containing ammonia, carbon dioxide, and water vapor is carried off from the top of the column, and a substantially urea-free aqueous solution of ammonia and carbon dioxide is removed from the bottom of the column. This substantially urea-free aqueous solution is subsequently expanded to a pressure of between about 1 and 5 bar, and ammonia and carbon dioxide are removed therefrom, for instance, by stripping with steam.

If the dilute aqueous solution to be treated in this process contains a relatively large quantity of ammonia, as would be the case, for instance, with process condensate formed in the preparation of urea as described above, a portion of this ammonia is preferably removed prior to introducing it into the reaction column. Such a solution would preferably first be introduced into a pre-desorption zone, operating at a pressure of between about 1 and 5 bar, wherein as much ammonia and carbon dioxide are removed as possible. Specifically, sufficient ammonia and carbon dioxide should be removed in the pre-desorption zone so that the ammonia and carbon dioxide concentration in the bottom of the reaction column will be sufficiently low as not to impede further hydrolysis of the very low urea concentration there present.

It has been found that the residence time in the reaction column and the quantity of gas for heating and stripping the solution to be treated in the reaction column must be considerably increased as the ammonia and/or carbon dioxide content in the feed solution increase, if urea and ammonia contents in the final solution of 10 ppm or less should be reached.

Preferably, the ammonia concentration of the dilute aqueous solution passed into the top of the reaction column should be no greater than about 3% by weight and still more preferably no greater than about 1% by weight.

In a preferred embodiment, the gas mixture removed from the top of the reaction column can be utilized as the heating and stripping agent in the pre-desoption zone. It is also possible to utilize the gas mixture formed in the post-desorption zone as a stripping agent in the predesorption zone. The heating and stripping agent used in the reaction column is preferably steam, having a pressure of between about 15 and 42 bar. Although other gases inert to the materials present in the column may be used as well, and fall within the scope of this invention, such other gases must be subsequently separated out, which will involve additional costs.

BRIEF DESCRIPTION OF THE DRAWING

The FIGURE illustrates an apparatus to carry out the inventive process.

DETAILED DESCRIPTION OF THE INVENTION

Figure 1:
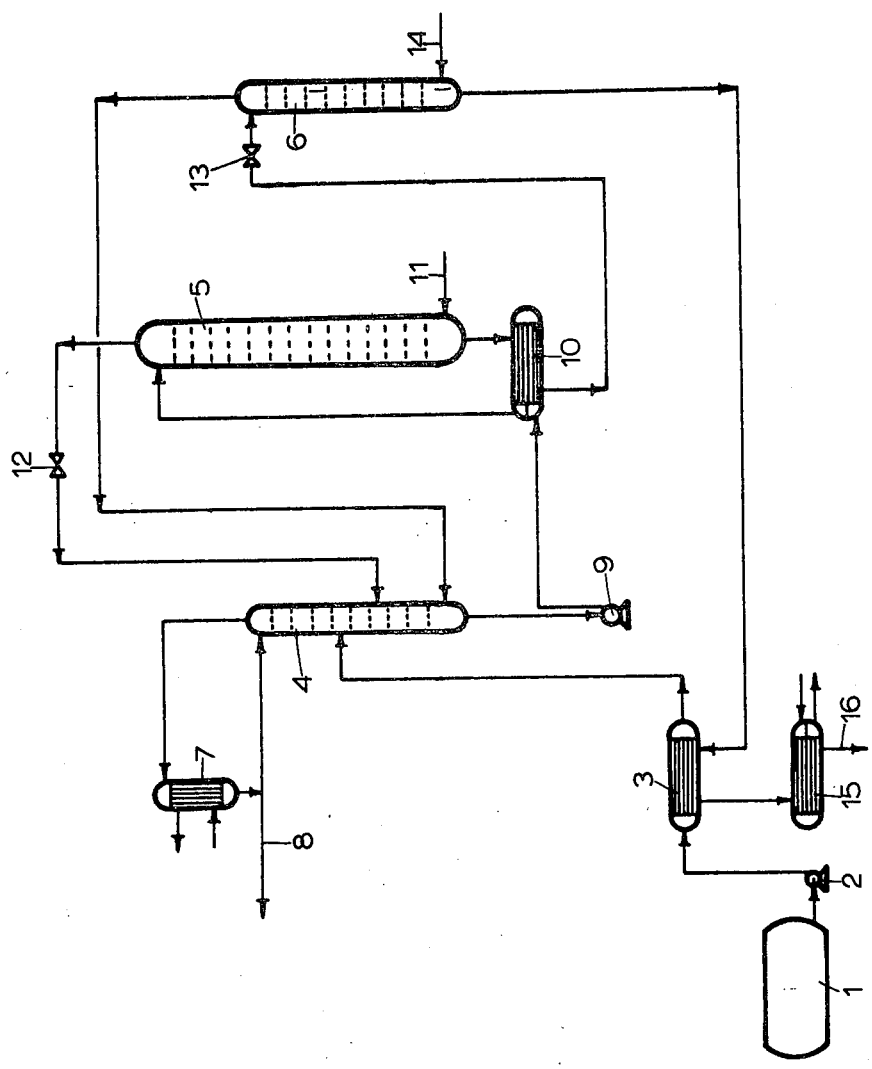

Referring to the FIGURE, process condensate collected in tank 1 is brought up to a pressure of between about 1 and 5 bar, for instance, 3 or 4 bar, by means of pump 2 and is passed, via heat exchanger 3, into bottom of the upper half of pre-desorption column 4. The off gases derived from the top of reaction column 5 and from post-desorption column 6 are introduced into the bottom portion of pre-desorption column 4, wherein the heat and stripping effect of these gases drives a major portion of the dissolved ammonia and carbon dioxide from the condensate. A predesorption column off gas thus formed, which also contains a quantity of water vapor, is completely condensed in reflux condenser 7. A small portion of the condensate is returned to the top of pre-desorption column 4, and the major portion of such condensate is passed through line 8 to a urea synthesis process wherein it may be used, for instance, in the condensation and absorption zone of the final decomposition step.

The liquid stream obtained from the bottom of pre-desorption column 4 still contains, in addition to relatively small quantities of ammonia and carbon dioxide, virtually the entire quantity of urea originally present. This liquid stream is subsequentially brought up to a pressure of between about 10 and 30 bar by means of pump 9, for instance 12.5 bar, is heated in heat exchanger 10, and is introduced into the top of reaction column 5. Reaction column 5 is divided, for instance by sieve plates, into a number of compartments which serve as gas bubble mixers. Instead, other types of gas-liquid contacting columns, e.g. those with bubble cap trays may be used. In principle packed columns can also be used, but are less recommendable because of the risk of channeling which would impede the hydrolysis of urea and the stripping of ammonia and carbon dioxide. A stripping and heating gas stream, preferably steam, is passed into the bottom of reaction column 5 through line 11 at a pressure of between about 15 and 42 bar, for instance 25 bar. Other vapors or gases, such as e.g. nitrogen, may be applied but would have to be separated from the gas mixture containing the ammonia and the carbon dioxide. The temperature profile over the length of the reaction column 5 is established by controlling the quantity of steam introduced, and the pressure in the reaction column, so that the top temperature is between about 170° and 220° C., and the bottom temperature is between about 180° and 230° C.

For instance, at a column pressure of 12.5 bar, a top temperature of 181° C. and a bottom temperature of 193° C. are maintained, with an average temperature of about 185° C.

The gas stream introduced through line 11 into the bottom of reaction column 5 supplies the heat necessary for the hydrolysis of urea and the evaporation of the ammonia and carbon dioxide released by the hydrolysis. The urea content of the solution flowing downward in reaction column 5 decreases fairly rapidly, more rapidly as the temperature increases. It has been found that after a certain residence time, the final urea concentration levels off, and is determined by the ammonia and carbon dioxide concentrations present in the liquid. For this reason, the predesorption of ammonia and carbon dioxide is often necessary to reach the required low urea content of 10 ppm or lower. The residence time of the liquid in reaction column 5 is generally in the range of between about 25 and 95 minutes. Residence time of less than 25 minutes are possible. However, in that case the construction costs are considerably higher because of the higher pressure and temperatures required, the latter involving a substantial increase of the corrosiveness of the solution to be treated. Residence times longer than 95 minutes would allow comparatively low average temperatures but require larger reaction columns and thus also higher investment costs. Suitable residence time are in the range of from 25 to 75 minutes. For instance, at an average temperature of 185° C., a minimum residence time in the reaction column of 70 minutes is necessary.

The reaction column off gas, comprised of the stripping agent and the gases driven off in the column, is removed from the top portion of reaction column 5 and, after expansion in pressure reducing device 12 to the pressure at which predesorption column 4 is operated, is introduced therein. This reaction column off gas is passed into pre-desorption column 4 at a point some distance below the supply of the process condensate to column 3 so the gas stream can give off part of its heat contents to the liquid condensate flowing down through the column.

The reaction column liquid collecting in the bottom of reaction column 5 still contains some dissolved ammonia and carbon dioxide, but is substantially free of urea. This reaction column liquid stream is passed through heat exchanger 10 wherein it is utilized to preheat the dilute aqueous solution fed into column 5. This reaction column liquid stream is thereafter expanded in pressure reducing device 13 to a pressure of between about 1 and 5 bar, for instance 3.5 bar, and is introduced into the top portion of post-desorption column 6. In post-desorption column 6, the mixture of gaseous ammonia, carbon dioxide, and water vapor released as a result of the expansion is immediately separated off, and the remaining liquid flows downward, countercurrent to a quantity of steam introduced through line 14. The quantity and heat content of the steam introduced through line 14 is sufficient to evaporate and drive off sufficient ammonia and carbon dioxide to reach the desired ammonia content of 10 ppm or lower.

The post-desorption column off gas, containing ammonia, carbon dioxide, and entrained water vapor, are passed from the top of column 6 to the bottom of pre-desorption column 4 wherein it serves, together with the reaction column off gas, as the heating and stripping agent for the liquid treated in pre-desorption column 4. The waste water flow from the bottom of post-desorption column 6 has a urea and ammonia concentration of 10 ppm or lower. A portion of the heat present in this waste water is recovered in heat exchanger 3 for pre-heating the liquid to be treated in pre-desorption column 4. The waste water flow is then optionally cooled in cooler 15 with cooling water, and finally discharged through line 16.

A preferred embodiment of this invention will be illustrated by means of the following example.

EXAMPLE

Process condensate obtained from a urea plant, having a production capacity of 1,500 tons per day, was treated by means of the improved process of this invention. All quantities are given in kilograms per hour, and all percentages are percent by weight.

Process condensate in an amount of 28,333 kg, containing 4.38 percent $NH_3$, 2.95 percent $CO_2$, and 1.09 percent urea, was heated in heat exchanger 3 from 42° C. to 125° C. This process condensate solution was introduced into pre-desorption column 4 wherein it was passed, at a pressure of 3.43 bar, countercurrently against first 1,147 kg of the off gas from reaction column 5, and subsequently 5,562 kg of the off gas from post-desorption column 6. The off gas from reaction column 5 consisted of 66 kg $NH_3$, 252 kg $CO_2$, and 829 kg of water vapor, and had a temperature of 181° C. The off gas from post-desorption column 6 had a composition of 421 kg $NH_3$, 5 kg of $CO_2$, and 5,136 kg of water vapor, at a temperature of 136° C.

The pre-desorption column off gas removed from the top of column 4 contained 2,293 kg of $NH_3$, 1,720 kg of $CO_2$, and 2,528 kg of water vapor. This pre-desorption column off gas was completely condensed and cooled to a temperature of 54° C. A portion of this condensed off gas, consisting of 876 kg of $NH_3$, 657 kg of $CO_2$, and 966 kg of water was returned as reflux to th desorption column. The remaining portion of this condensed off gas, containing 1,562 kg of water, 1,417 kg of $NH_3$, and 1,063 kg of $CO_2$, was returned to the urea plant. Thus, in pre-desorption column 4, 75 percent of the quantity of ammonia originally present was removed.

The desorbed solution leaving the bottom of pre-desorption column 4, in addition to 30,349 kg of water, contained 310 kg of $NH_3$, 31 kg of $CO_2$, and 319 kg of urea. This solution was brought up to a pressure of 12.26 bar by means of a pump 9, heated from 135° C. to 183° C. in heat exchanger 10, and thereafter introduced into the top portion of reaction column 5. An amount of 1,700 kg of steam, having a temperature of 225 C. and a pressure of 24.5 bar, was introduced into the bottom of reaction column 5, and passed countercurrently against the downward flowing solution. The urea present in the feed solution was hydrolyzed almost completely to ammonia and carbon dioxide. The reaction column off gas, containing ammonia and carbon dioxide, was removed from column 5 and expanded from 14.7 bar to 3.43 bar in expansion device 12.

The reaction column liquid stream leaving the bottom of column 5 consisted of 31,127 kg of water, 419 kg of $NH_3$, and 6 kg of $CO_2$. This liquid stream was used for pre-heating the feed stream of the reaction column, and in so doing its temperature decreased from 193° C. to 146° C. The pressure of this liquid stream was reduced to 3.43 bar by expansion in the top of post-desorption column 6, which resulted in a further temperature decrease to 136° C. In post-desorption column 6, this solution was stripped with 5,000 kg of steam having a temperature of 147° C., resulting in the formation of 5,562 kg of a gas mixture. This post-desorption column off gas was then introduced into the bottom of pre-desorption column 4. The liquid stream removed from the bottom of post-desorption column 6 was first used to preheat the process condensate to be treated in accordance with this process, resulting in its temperature decrease from 135° C. to 63° C., and it was subsequently cooled with cooling water to 40° C., upon which it was discharged from the process. This waste water liquid phase leaving the process contained 6 ppm ammonia and 8 ppm urea.

What is claimed is:

1. In a process for the removal of urea, ammonia, and carbon dioxide from a dilute aqueous solution thereof by hydrolyzing said urea and thereafter desorbing ammonia and carbon dioxide, comprising the steps of:

introducing said dilute aqueous solution into a pre-desorption zone wherein a portion of said ammonia and carbon dioxide is removed therefrom to form a pre-desorption zone off gas containing ammonia, carbon dioxide and water vapor, and a pre-desorption zone liquid stream comprised of a dilute aqueous solution of urea, ammonia, and carbon dioxide;

introducing said pre-desorption zone liquid stream into a reaction column wherein it is contacted with steam introduced into the bottom of said reaction column, while maintaining said reaction column under pressure;

removing from said reaction column a reaction column of gas comprised of a gas mixture containing ammonia, carbon dioxide and water vapor, and a reaction column liquid stream comprised of a substantially urea-free aqueous solution of ammonia and carbon dioxide;

introducing said reaction column liquid stream into a post-desorption zone wherein ammonia and carbon dioxide are removed therefrom to form a post-desorption zone off gas and a residual post-desorption zone liquid stream;

introducing said reaction column off gas and said post-desorption zone off gas into said pre-desorption zone; and condensing said pre-desorption zone off gas to form a dilute aqueous solution of ammonia and carbon dioxide, at least a portion of which is thereafter used in a process for the preparation of urea;

the improvement comprising:

lowering the ammonia content of said dilute aqueous solution in said pre-desorption zone, at a pressure of between about 1 to and 5 bar, to about 3% by weight or less;

introducing steam having a pressure of between about 15 and 42 bar into said reaction column, and causing the said pre-desorption zone liquid stream to flow downward in said reaction column countercurrent to said steam while maintaining said reaction column at a pressure of between about 10 and 30 bar, and at a top column temperature of between about 170° and 220° C. and a bottom column temperature of between about 180° and 230° C., while maintaining the residence time of said dilute aqueous solution in the reaction column in the range of between about 25 and 95 minutes;

removing said reaction column off-gas from the top of said reaction column and removing said reaction column liquid stream from the bottom of said reaction column;

introducing said reaction column off gas into said pre-desorption zone at a point in such zone between the respective points of supply of said dilute aqueous solution and said post-desorption zone off gas to such zone;

maintaining in said post-desorption zone a pressure of between about 1 and 5 bar; and discharging from said post-desorption zone a post-desorption liquid-stream having a urea content and an ammonia content of at most 10 ppm each.

2. The process of claim 1 wherein, in said post-desorption zone, ammonia and carbon dioxide are removed from said reaction column liquid stream by countercurrent stripping with steam.

3. The process of claim 1 wherein said dilute aqueous solution of urea, ammonia, and carbon dioxide passed into the top portion of said reaction column is first preheated by heat exchange with said reaction column liquid stream.

4. The process of claim 1, wherein the ammonia content of the dilute aqueous solution in the predesorption zone is lowered to below about 1% by weight.

* * * * *